(12) United States Patent
Berg

(10) Patent No.: US 6,411,380 B1
(45) Date of Patent: Jun. 25, 2002

(54) DETECTION DEVICE FOR A SPECTROPHOTOMETER

(75) Inventor: Björn Berg, Kungsängsgatan (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/125,921

(22) PCT Filed: Feb. 18, 1997

(86) PCT No.: PCT/SE97/00264

§ 371 (c)(1),
(2), (4) Date: Jun. 7, 1999

(87) PCT Pub. No.: WO97/31246

PCT Pub. Date: Aug. 28, 1997

(30) Foreign Application Priority Data

Feb. 22, 1996 (SE) .............................................. 9600666

(51) Int. Cl.[7] .............................. G01J 3/02; G01J 3/42
(52) U.S. Cl. ........................................................ 356/319
(58) Field of Search ................................. 356/319, 326, 356/328

(56) References Cited

U.S. PATENT DOCUMENTS

| 4,145,689 A | * | 3/1979 | Bultler et al. ................ 341/136 |
| 4,940,983 A | * | 7/1990 | Jones et al. .................. 341/171 |
| 5,014,216 A | * | 5/1991 | Stafford et al. ............. 356/328 |

* cited by examiner

Primary Examiner—F L Evans
(74) Attorney, Agent, or Firm—Royal N. Ronning, Jr.; Robert F. Chisholm; Stephen G. Ryan

(57) ABSTRACT

The present invention relates generally to a detection device for a spectrophotometer system, and in particular to a light detection device with an analogue input and a digital output. The object of the present invention is to provide a more accurate detection device, which requires substantially less space for accommodating the detection device in a spectrophotometer. This object is solved by using a successive approximation A/D converter (16) which has internal sample and hold circuits, and which heretofore has been used in the audio industry. This will increase the accuracy of the detection device and make it more resistant against disturbances. It will also decrease the space required for such detection device, down to one third compared to conventional detection devices.

20 Claims, 1 Drawing Sheet

DETECTION DEVICE FOR A SPECTROPHOTOMETER

BACKGROUND OF THE INVENTION

1. Field of the Invention

The present invention relates generally to a detection device for a spectrophotometer system, and particularly to a light detection device with an analogue input and a digital output.

2. Description of the Prior Art

In a spectrophotometer system the concentration of a substance in a test sample is measured. Such a system generally comprises a continuous light source, optical elements and a detection device for detecting a test sample beam of light and/or a reference beam of light. The advantage of detecting both a test and a reference beam of light, i.e. with a two channel system, is that the measurement of the concentration of the substance is made independently of the variations of the light source. In a two channel system the test sample beam first enters a flow cell, through which test samples are passed from a chromatographic column, and then impinges on a first detector with an intensity I and the reference beam impinges directly, via optical elements, on a second detector with an intensity $I_0$.

The detector output signals are then processed in the detection device to firstly calculate the absorbency of light in the test sample in accordance with the well known equation, $$A = -\log(I/I_0)$$

Thereafter the concentration in the test sample is calculated by using the following equation, $$A = \in * 1 * C$$

where 1 is the path length of the flow cell, C is the concentration and $\in$ is the absorbability.

U.S. Pat. No. 4,678,917 describes a multichannel spectrophotometer comprising an array of photo detectors for obtaining data for a wide spectrum chromatogram. The signals output by the photo detectors enter sample and hold circuits before they, via a multiplexor switch, are converted by an A/D-converter. The radiation source is a deuterium lamp sending out continuous radiation through a sample cell. The object of this invention is to provide a simultaneous measurement for a wide spectrum light, rather than for only one wavelength.

U.S. Pat. No. 4,318,618 describes an apparatus for automatically measuring changing values of absorbency. The described system is a two channel system having one measuring and one reference photo detector. The signals coming from the photo detectors are digitised via I/V converts and A/D converts before they are processed. The object of this invention is to secure that the absorption cell in which the sample is contained is aligned in a measuring zone in order to provide an accurate measurement.

U.S. Pat. No. 5,387,979 shows another example of a two channel spectrophotometer system. This system uses a pulsating (modulated) source of radiation giving rise to an alternating current component. This reduces the measurement response time of the for changes in the concentration of the specific substance measured.

U.S. Pat. No. 4,549,809 shows a one channel photometric measurement method, wherein readings are taken at precisely measured intervals as a function of the width of the cuvette and at the same distance from the leading wall of each cuvette containing the test sample.

The detection devices for the spectrophotometers in the above described U.S. Pat. Nos. generally comprise detectors, such as photo cells, integrator means, amplifying means, analogue to digital (A/D) converters, buffering means and evaluation means, such as a microprocessor or computer.

The A/D converters that are used for such a detection device traditionally use external sample and hold circuits prior to the converter. This causes problems, firstly in that the lines between the sample and hold circuits are subject to interferences and thus the accuracy of the A/D conversion deteriorates. Secondly the sampling speed will be affected negatively by using external sample and hold circuits. This again will deteriorate the accuracy of the A/D conversion due to dark currents and charge injections.

The A/D converters in detection devices used for spectrophotometers are specially designed and therefore manufactured in small series, and hence expensive. The advantage of these specially designed A/D converters is that they have many options and can be adapted to all kinds of signals.

Since there are two signals that have to be converted in the detection device for the spectrophotometer, i.e. the reference signal and the test sample signal, two such A/D converters are required. Furthermore, these A/D converters require several additional control circuits to operate properly, due to all the available options mentioned above, and therefore require a large space. Thus, there is a need for an accurate A/D converter that is less space consuming and much cheaper in order to bring down the overall size and cost for the detection device.

The above mentioned U.S. Patents furthermore all comprise a radiation source sending out radiation continuously giving rise to dynamic output waveforms from the photo detectors, in which waveforms the peak values have to be determined in order to get an accurate measurement. The continuous radiation does furthermore not prescribe any high demands on the sampling frequency.

SUMMARY OF THE INVENTION

Accordingly, the object of the present invention is to provide a more accurate detection device, which requires substantially less space for accommodating the detection device in a spectrophotometer and also to reduce the manufacturing cost of such a device.

This object of the invention is solved by the device using a successive approximation A/D converter with an internal sample and hold circuit, which heretofore has been used in the audio industry, for example in DAT-tape recorders and other studio equipments. The use of such an A/D converter substantially reduces the space needed for the detection device, down to one third of the space required for a conventional detection device. The configuration of such an A/D converter with an internal sample and hold circuit enhances also the accuracy and the speed of the converter. Furthermore such an A/D converter is much cheaper, since it is mass produced.

The A/D converter according to the present invention is controlled by a sequence generator in order to secure proper functioning of the A/D converter in the detection device for the spectrophotometer.

To further improve the accuracy of the detection device the radiation source is a flash generating source giving rise to a step response from the photo detectors, of which step response only the start and end values need to be measured.

BRIEF DESCRIPTION OF THE DRAWINGS

In the following the invention is described in greater detail with the help of a preferred exemplifying embodiment with reference to the accompanying drawing in which.

DESCRIPTION OF THE PREFERRED EMBODIMENTS

Figure 1:
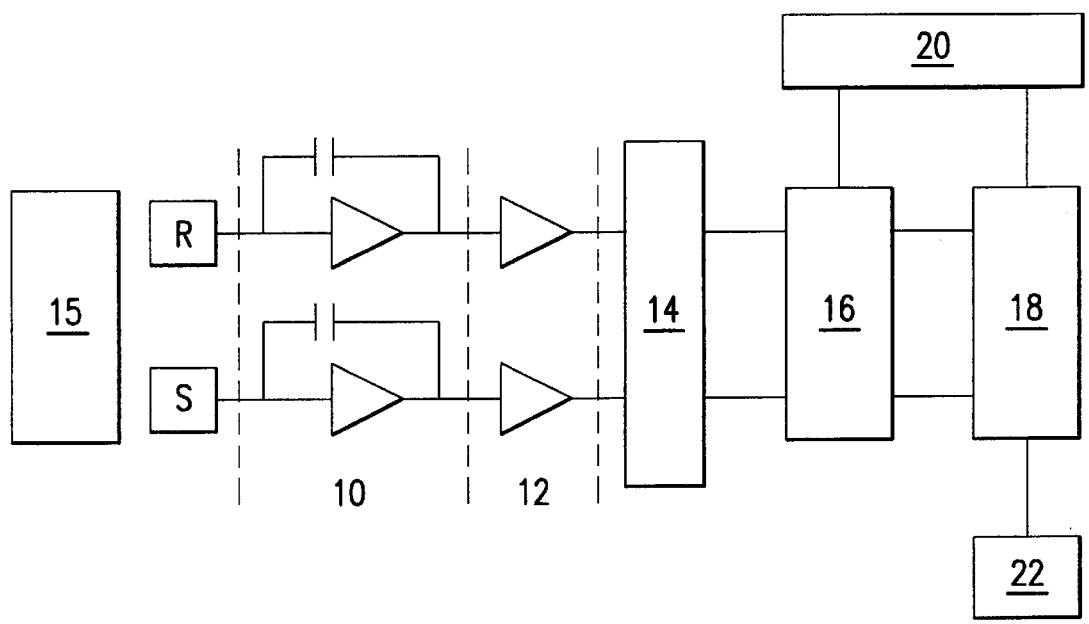
FIG. 1 shows an embodiment of the detection device according to the present invention.

FIG. 1 shows a detection device for a spectrophotometer according to the present invention. The detection device comprises two sensing means R and S, for example photo cells or other light sensing devices, integrator means 10, amplifying means 12, filtering means 14, a successive approximation A/D converter 16, buffering means 18, sequence generating means 20 and evaluating means 22, such as a microprocessor or computer.

It should be noted that even if the radiation source 15, which sends out the radiation to be sensed by the photo detectors, is not in itself a part of the detection device, its way of operating will influence the design of the detection device. Compared to the above cited prior art the detection device of the present invention is designed for use together with a flash generating source and not together with a traditionally continuous radiation source. The use of a flash generating source will give rise to a step response from the photo detectors instead of a traditional continuous waveform.

The two photo cells R and S are used to measure the light beams of the generated flash that impinge thereon, said light beams coming from the same light source (not shown). The reference photo cell R detects the unaffected light coming from the light source, whereas the signal photo cell detects the light that has passed a flow cell, through which the test sample flows, whose concentration of a certain substance is to be measured. The outputs of the photo cells R and S will have an output current, i.e. the difference between the start and end current values of the step response, that is proportional to the amount of light impinging thereon.

The output current step responses from the photo cells are then fed to an integrator step 10 in which the currents are integrated. Since there are two currents to be integrated this step comprises two separate integrators. The integrators comprise an operational amplifier and a capacitor as is well known in the art.

The integrated currents are thereafter amplified in an amplifying step 12. This step comprises two separate programmable amplifiers. Each separate amplifier consists of two cascade connected programmable amplifiers, such as AD 526.

Before the two detected signals enter the A/D converter 16 they are passed through filtering means 14. Since the measuring range of the A/D converter 16 is between −2.7 and 2.7 volts and does not tolerate voltages outside the range of −5 to 5 volts, the signals leaving the amplifying step 12 have to be adapted in order to protect the A/D converter 16 and to keep the signal within the measuring range of the A/D converter 16. This is done by a second degree Butterworth filter and by applying an offset to the signal before it enters the A/D converter 16. The filtering means 14 also comprise an overvoltage protection so that the A/D converter 16 never can be fed with a signal that would damage it.

The A/D converter 16 is a successive approximation converter, such as PCM1750 from Burr-Brown, which heretofore has been used in the audio industry. This A/D converter 16 is configured with internal sample and hold circuits, which enhance the accuracy and the speed of the converter. Furthermore, the use of this A/D converter 16 will substantially reduce the space needed for the detection device, down to one third of the space required for a conventional detection device. This A/D converter 16 has two separate channels which are clocked and trigged simultaneously by means of sequence generating means 20. The control signals for the A/D converter 16 are normally generated by a digital filter comprised in the A/D converter 16, but since the present invention does not use the linear filtration of the signal, the control signals have to be generated by said sequence generating means 20.

The sequence generating means 20 controls the whole measuring and trigger procedure. It comprises two sequence generators, one slow sequence generator comprising a counter and a PROM and a fast sequence generator. The slow sequence generator controls among other things the start of the A/D conversion and also control functions for the fast sequence generator. The fast sequence generator controls the A/D converter and the data flow coming out from it. It is believed that the design of the sequence generator 20 is within the skills of the man in the art and design details are therefore left out for the sake of simplicity.

After the conversion the data are fed to a first in first out (FIFO) memory 18 via address controlled digital ports (not shown), such as two 8 bit latches, that clock the data. The FIFO 18 comprises a series to parallel converter which groups the data from both channels and then alternately writes the data into the FIFO memory 18. Also the FIFO memory 18 is controlled by the sequence generating means.

At the end of the measuring sequence the data is the transferred from the FIFO 18 to the microprocessor 22.

Figure 2:
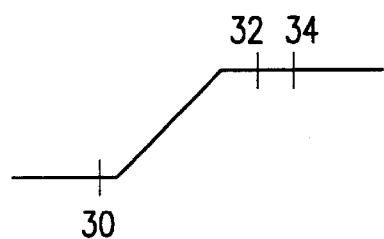
FIG. 2 shows the step response generated by the sensing means, the signal of which is to be measured.

FIG. 2 shows the step response generated by the sensing means R and S, the signal of which is to be measured and of which the essential parts 30, 32, 34 are to be converted by the A/D converter 16. Since the object of a spectrophotometer is to determine the concentration of a certain substance in a test sample only the start and the end values of the step response are of interest. The sequence generating means 20 has a number of prestored measuring sequences which can be selected by a user.

The measuring sequence starts with the generating of a flash from the light source. This will cause the step response according to FIG. 2. The sequence generating means 20 will control the A/D converter to take samples at 30. Depending on which sequence the user has selected the number of samples will vary. Preferably eight, sixteen or even more samples are taken and converted by the A/D converter. The reason why at least 8 samples are taken is to eliminate the effect of noise and other disturbances.

The user could of course also select a smaller number of samples, but this would affect the accuracy negatively.

In a corresponding way the sequence generating means 20 controls the sampling at 32 and 34 at the end of the step response. These sampled and converted data are then transferred to the microprocessor 22 via the FIFO memory 18 as mentioned above. The measuring sequence is terminated when the FIFO memory 18 has received the data. This enables a new measuring sequence to be started while the microprocessor 22 processes the data.

The microcomputer 22 averages the values for each measuring point 30, 32 and 34 and then calculates the concentration of the substance in question in the test sample.

Even though the present invention has been described with one exemplifying embodiment, it is believed that the man skilled in the art can make changes and modifications of the present invention without departing from scope of the invention, which is only limited by the attached claims.

What is claimed is:

1. A detection device for a spectrophotometer, said device having an analogue input and a digital output and comprises sensing means (R, S), integrator means (10), amplifier means (12), and A/D converter (16), and buffering means (18), all connected in series, and evaluation means (22), characterised in that said A/D converter (16) has internal sample and hold circuits and further comprising sequence generating means (20) for controlling sampling and conversion of a step response generated by said sensing means (R, S).

2. A detection device according to claim 1, comprising two separate measuring channels, one of which measures a reference signal and the other measures a signal affected by a test sample and wherein said evaluation means (22) comprises means for determining the absorbency of light in said test sample.

3. A detection device according to claim 2, wherein said sequence generating means generates clock signals to trigger said A/D converter to take samples of said reference signal and sample signal.

4. A detection device according to claim 1, wherein said sequence generating means is pre-set with at least one measuring sequence comprising at least two measuring points (30, 32) of said step response.

5. A detection device according to claim 4, wherein said measuring points (30, 32, 34) each comprises several samples of said step response.

6. A detection device according to claim 1, wherein the A/D converter (16) is a successive approximation converter.

7. A detection device according to claim 1, further comprising filtering means (14) connected between said amplifying means (12) and said A/D converter (16) for protecting said A/D converter (16) from overvoltages.

8. A detection device according to claim 1, wherein said buffering means comprises a series to parallel conversion and a first-in/first-out memory (18).

9. A detection device according to claim 2, wherein said evaluating means (22) is a microprocessor for calculating the concentration of a detected substance in said test sample.

10. A spectrophotometer system, characterised by a detection device according to claim 1.

11. A detection device according to claim 6, further comprising a radiation source.

12. A detection device according to claim 11, wherein said radiation source further comprises a flash generating radiation source for providing a step response from said sensing means.

13. A detection device according to claim 12, wherein said sensing means further comprises a first and second photo detector.

14. A detection device according to claim 13, wherein said first photo detector further comprises a reference photo cell and said second photo detector further comprises a signal photo cell.

15. A detection device according to claim 14, wherein said integrator means further comprises a first and second integrator.

16. A detection device according to claim 15, wherein said amplifier means further comprises a first and second programmable amplifier.

17. A detection device according to claim 16, further comprising a filtering means serially connected between said amplifier means and said A/D converter, wherein said filtering means includes overvoltage protection circuitry to protect said A/D converter.

18. A detection device according to claim 17, wherein said A/D converter further comprises a first and second channel, said first and second channels being clocked and triggered by said sequence generating means.

19. A detection device according to claim 18, wherein said sequence generating means further comprises a slow sequence generator and a fast sequence generator, wherein said slow sequence generator further comprises a counter and a PROM.

20. A detection device according to claim 19, wherein said buffering means comprises a series to parallel conversion and a first-in/first-out memory and wherein said evaluating means is a microprocessor for calculating the concentration of a detected substance in a test sample.

* * * * *